United States Patent [19]

Mohs et al.

[11] Patent Number: 4,855,101

[45] Date of Patent: Aug. 8, 1989

[54] PROCESS FOR COATING PROSTHESES OF TITANIUM AND TITANIUM ALLOYS

[75] Inventors: Rudolf Mohs; Günter Bensmann, both of Essen, Fed. Rep. of Germany

[73] Assignee: Fried. Krupp GmbH, Fed. Rep. of Germany

[21] Appl. No.: 213,942

[22] Filed: Jul. 1, 1988

[30] Foreign Application Priority Data

Jul. 17, 1987 [DE] Fed. Rep. of Germany ....... 3723650

[51] Int. Cl.$^4$ .............................................. G22F 7/00
[52] U.S. Cl. ......................................... 419/8; 419/23; 419/35; 419/60; 623/16
[58] Field of Search .......................... 419/60, 8, 23, 35; 623/16

[56] References Cited

U.S. PATENT DOCUMENTS

| | | |
|---|---|---|
| 3,417,461 | 12/1968 | Wells et al. ............................ 29/487 |
| 4,599,085 | 7/1986 | Riess et al. ............................... 419/8 |
| 4,644,942 | 2/1987 | Sump ........................................ 419/8 |
| 4,714,468 | 12/1987 | Wang ...................................... 419/28 |

FOREIGN PATENT DOCUMENTS 2534113 2/1977 Fed. Rep. of Germany .

Primary Examiner—Stephen J. Lechert, Jr.
Attorney, Agent, or Firm—Sughrue, Mion, Zinn, Macpeak & Seas

[57] ABSTRACT

Particles are sinter-fused onto the surface of a prosthesis shaft of titanium or titanium alloys. Before sinter-fusing, a coating material which forms below the $\alpha$-$\beta$-transition temperature a liquid phase with the material of the prosthesis and particles is applied to provide a coating between the shaft and particles.

12 Claims, No Drawings

PROCESS FOR COATING PROSTHESES OF TITANIUM AND TITANIUM ALLOYS

BACKGROUND OF THE INVENTION

The present invention relates to a process for coating a prosthesis made of titanium or a titanium alloy, and more particularly relates to coating such a prosthesis by sinter-fusing coating.

Currently endoprostheses are mostly fixed with bone cement into the prepared prosthesis position. This method of attachment has recently encountered more and more criticism, as the system "metallic prosthesis/bone cement/bone" does not have sufficient durability, with the consequences that the prostheses implanted in this manner loosen.

For this reason it has been tried for some time to fix prostheses in the bone without cement. In order to attain in this case a good contact between bone and implant, efforts are made to produce prostheses with a structured surface. Such prostheses can basically be produced by lost-wax casting or by sinter coating an already shaped prosthesis with particles made from the same type of material as the already shaped prosthesis to provide a grainy coating. In the case of prostheses of titanium alloys the process is, as now known, to sinter-fuse particles onto a forged prosthesis or onto a prostheses produced by a chip removal process.

The disadvantage with this process is that a sufficient fastening of, e.g., titanium spheres or balls onto a titanium shaft by sintered heat treatment can only be attained at temperatures clearly above the $\alpha$-$\beta$-transition temperature. A coating above this temperature has the effect that the working material (the material of the shaft) becomes coarse grained and looses the good mechanical properties which it possessed in its starting condition before the sinter-fusing.

Thus, there are described, e.g., in St.A. Cook, "Fatigue properties of carbon- and porous-coated Ti-6Al-4V alloy", Journal of Biomedical Materials Research, Volume 18, 2. 497 to 512, 1984, investigations of the bending fatigue endurance limit of untreated and coated samples of the titanium alloy Ti-6Al-4V, often used as implant material, proving that the bending fatigue endurance limit of the untreated titanium alloy of 617 N/mm$^2$ drops with coating by sintered heat treatment to 138 N/mm$^2$. The drop in endurance can be attributed to the superposition of two effects: on the one hand, the coarsening of the grain by heat treatment above the transition temperature and, on the other hand, the surface structure which improves the notch stress. For this reason, samples were also tested which were subjected to the temperature cycle of the heat treatment of the coating process, but were not coated. In these tests a bending fatigue endurance limit of 377 N/mm$^2$ was determined. This proves that a large part of the reduction in bending fatigue endurance limit of titanium alloys can be attributed to the coarsening of the grain by the coating process executed above the transition temperature.

SUMMARY OF THE INVENTION

Consequently, it is an object of the present invention to provide a process for producing a prosthesis which employs a coating process that is executed below the $\alpha$-$\beta$-transition temperature.

A further object of the present invention is to provide such a process in which there is still achieved a solid contact between the coated particles and basic working material of the prosthesis, so that the prosthesis coated in this manner has a considerably higher bending fatigue endurance limit than up to now.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects and in accordance with its purpose, the present invention provides a process for sinter-fusing particles onto the surface of a prosthesis shaft made of titanium or a titanium alloy for better bone fusion, the particles having a composition which is of the same type of basic material composition of the shaft. The same type of basic materials are titanium alloys and all grades of pure titanium. The process comprises providing a coating between the particles and shaft before the sinter-fusing, the coating being of a material which forms below the $\alpha$-$\beta$-transition temperature a liquid phase with the material of the prosthesis and the particles.

The coating can be achieved by coating the particles with the coating material or by coating the shaft with the coating material. The particles preferably are in the form of small spheres or balls with a defined diameter, preferably between 300 to 800 $\mu$m. Preferably, the particles are coated with a thin layer of the coating material-the thickness of the coating is approximately between 1 and 5 $\mu$m. In a preferred embodiment of the present invention, the coating material is copper.[1]

[1] and it is fixed on the surfaces by a electrochemical process

The sinter-fusing of the particles is preferably done under vacuum or a protective gaseous atmosphere, which is free of hydrogen, oxygen and nitrogen. For copper coated particles, a sinter-fusing temperature of approximately 880° C. to 950° C. is particularly suitable. The actual sintering process suitably lasts 1 to 10 hours.

Preferably, the particles are attached to the prosthesis shaft before sinter-fusing by means of a suitable synthetic material adhesive, e.g., acetone diluted Plexigum[2]. This has the effect that the particles do not shift during the sinter coating process.

[2] Plexigum is a trademark of Röhm & Haas, Harmstadt, Germany

It is to be understood that both the foregoing general description and the following detailed description are exemplary and explanatory, but are not restrictive of the invention.

DETAILED DESCRIPTION OF THE INVENTION

The subject of the invention is explained in the following example:

Titanium or titanium alloy particles in the form of spheres of approximately 500 $\mu$m diameter, produced, e.g., by atomization, are coated with a thin layer of copper, approximately 2 $\mu$m thick. Then, the coated titanium alloy particles are attached to a titanium or titanium alloy body in one or more layers with Plexigum, diluted with acetone, and sintered for 2 hours at 920° C. in vacuum below the $\alpha$-$\beta$-transition temperature. During this sintering process a liquid TiCu phase is produced which forms enlarged contact zones by adhesion on the originally dot-shaped contact areas between the Ti or Ti alloy spheres and the titanium or titanium alloy body, leading to a good adhesion between the Ti contacting spheres themselves and the Ti containing spheres and the titanium or titanium alloy body.

Depending on the duration of this sintering process, the Cu, while forming various phases, diffuses into the spheres and into the titanium or titanium alloys body and can then be shown only in very low concentrations on the surfaces.

The titanium or titanium alloy body can be coated with a single layer of the particles or with more than one layer of particles, such as two layers of particles. When a single layer of particles is used to coat the titanium or titanium alloy body, it is sufficient to coat only this body with the liquid phase-forming coating material. Thus, for example, a copper layer can be applied directly to the titanium or titanium alloy body, and then the titanium containing particles can be placed on the copper layer and the entire structure subjected to sinter fusing.

It will be understood that the above description of the present invention is susceptible to various modifications, changes and adaptations, and the same are intended to be comprehended within the meaning and range of equivalents of the appended claims.

What is claimed is:

1. Process for sinter-fusing titanium particles or titanium alloy particles onto the surface of a prosthesis shaft made of titanium or a titanium alloy for better bone fusion, comprising providing a coating between the particles and the shaft before the sinter-fusing, the coating being of a material which forms below the $\alpha$-$\beta$-transition temperature a liquid phase with the material of the prosthesis and the particles, which is performed below $\alpha$-$\beta$-transition temperature.

2. Process according to claim 1, wherein the coating is provided by coating the particles with the coating material.

3. Process according to claim 2, wherein the particles are coated with copper as the coating material before sinter-fusing.

4. Process according to claim 2, wherein the sinter-fusing of the particles is done under vacuum.

5. Process according to claim 2, wherein the sinter-fusing of the particles is done in a protective atmosphere free of hydrogen, oxygen and nitrogen.

6. Process according to claim 2, wherein the particles are attached to the prosthesis shaft by a synthetic material adhesive before the sinter-fusing.

7. Process according to claim 6, wherein the adhesive is acetone diluted Plexigum.

8. Process according to claim 3, wherein the sinter-fusing of the particles is done under vacuum.

9. Process according to claim 3, wherein the sinter-fusing of the particles is done in a protective atmosphere free of hydrogen, oxygen and nitrogen.

10. Process according to claim 3, wherein the particles are attached to the prosthesis shaft by a synthetic material adhesive before the sinter-fusing.

11. Process according to claim 10, wherein the adhesive is acetone diluted plexigum.

12. Process according to claim 1, wherein the coating is provided by coating the shaft with the coating material.

* * * * *